(12) United States Patent
Higgins

(10) Patent No.: US 7,338,529 B1
(45) Date of Patent: Mar. 4, 2008

(54) METHODS AND APPARATUSES FOR ENHANCING PROSTHETIC IMPLANT DURABILITY

(75) Inventor: Joel C Higgins, Claypool, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 503 days.

(21) Appl. No.: 10/813,355

(22) Filed: Mar. 30, 2004

(51) Int. Cl.
A61F 2/38 (2006.01)

(52) U.S. Cl. ............................................ 623/20.14

(58) Field of Classification Search ............. 623/20.14, 623/20.29, 20.28, 20.15, 20.32, 20.33, 20.24
See application file for complete search history.

(56) References Cited

U.S. PATENT DOCUMENTS

| | | | |
|---|---|---|---|
| 3,338,805 A | 8/1967 | Pochily et al. | |
| 3,643,658 A | 2/1972 | Steinemenan | |
| 4,040,129 A | 8/1977 | Steinemann et al. | |
| 4,465,524 A | 8/1984 | Dearnaley et al. | |
| 4,511,411 A | 4/1985 | Brunner et al. | |
| 4,673,408 A | 6/1987 | Grobbelaar | |
| 4,687,487 A | 8/1987 | Hintermann | |
| 4,743,308 A | 5/1988 | Sioshansi et al. | |
| 4,790,851 A | 12/1988 | Suire et al. | |
| 5,037,438 A * | 8/1991 | Davidson | 623/22.15 |
| 5,057,108 A | 10/1991 | Shetty et al. | |
| 5,080,675 A * | 1/1992 | Lawes et al. | 623/20.33 |
| 5,169,597 A | 12/1992 | Davidson et al. | |
| 5,171,282 A | 12/1992 | Pequignot | |
| 5,197,987 A | 3/1993 | Koch et al. | |
| 5,308,412 A | 5/1994 | Shetty et al. | |
| 5,326,362 A | 7/1994 | Shetty et al. | |
| 5,334,264 A | 8/1994 | Meletis | |
| 5,358,530 A * | 10/1994 | Hodorek | 623/20.29 |
| 5,370,694 A * | 12/1994 | Davidson | 623/23.6 |
| 5,415,704 A | 5/1995 | Davidson | |
| 5,427,631 A | 6/1995 | Johansson et al. | |
| 5,562,730 A | 10/1996 | Davidson | |
| 5,593,452 A | 1/1997 | Higham et al. | |
| 5,683,468 A | 11/1997 | Pappas | |
| 5,755,802 A | 5/1998 | Gerber | |
| RE35,863 E | 7/1998 | Sachdeva et al. | |
| 5,811,194 A | 9/1998 | Kurze et al. | |
| 5,868,796 A | 2/1999 | Buechel et al. | |
| 5,879,388 A | 3/1999 | Pienkowski et al. | |
| 5,997,577 A | 12/1999 | Herrington et al. | |
| 6,187,045 B1 | 2/2001 | Fehring et al. | |
| 6,238,491 B1 | 5/2001 | Davidson et al. | |

(Continued)

*Primary Examiner*—Pedro Philogene
(74) *Attorney, Agent, or Firm*—Harness, Dickey & Pierce, P.L.C.

(57) ABSTRACT

The present teachings provide for a prosthetic implant comprising a femoral component, a tibial component, a bearing and a wear reduction device. The femoral component is operable to replace at least a portion of a patient's natural femur. The tibial component is operable to replace at least a portion of a patient's natural tibia, the tibial component having a superior tibial component surface. The bearing is operable to provide engagement between the femoral component and the tibial component. The bearing has a superior bearing surface operable to articulate with the femoral component and an inferior bearing surface operable to cooperate with the superior tibial component surface. The wear reduction device is located at least one of the superior tibial component surface and the inferior bearing surface and is operable to reduce wear upon at least one of the superior tibial component surface and the inferior bearing surface.

18 Claims, 2 Drawing Sheets

U.S. PATENT DOCUMENTS

| | | |
|---|---|---|
| 6,383,222 B1 | 5/2002 | Budorf |
| 6,506,215 B1 | 1/2003 | Letot et al. |
| 6,514,289 B1 * | 2/2003 | Pope et al. ................ 623/23.6 |
| 6,558,421 B1 | 5/2003 | Fell et al. |
| 6,645,251 B2 * | 11/2003 | Salehi et al. ............. 623/20.28 |
| 2002/0013625 A1 | 1/2002 | Abouaf et al. |
| 2002/0107578 A1 | 8/2002 | Speitling et al. |
| 2002/0183850 A1 | 12/2002 | Felt et al. |
| 2002/0198601 A1 | 12/2002 | Bales et al. |
| 2003/0028254 A1 | 2/2003 | Hunter et al. |
| 2005/0027365 A1 * | 2/2005 | Burstein et al. ......... 623/20.32 |

* cited by examiner

METHODS AND APPARATUSES FOR ENHANCING PROSTHETIC IMPLANT DURABILITY

FIELD

The present teachings relate to prosthetic implants. In particular, the present teachings relate to various methods and apparatuses for reducing wear between two prosthetic components.

BACKGROUND

A wide variety of different prosthetic implants and implant systems exist for replacing and/or repairing bone and/or tissue. An exemplary implant system is described in U.S. Pat. No. 6,165,223, which is incorporated by reference. Many of these conventional implants and/or implant systems include one or more moving components. While such conventional implants are well suited for their intended uses, it would be advantageous to reduce wear that might occur between components. For example, in conventional fixed and mobile prosthetic knee joints it would be advantageous to reduce wear that might occur between the tibial component and the bearing positioned between the femoral component and the tibial component, the wear being more pronounced in mobile joints but still often present in fixed joints due to micro-motion movement between the bearing and the tibia.

SUMMARY

The present teachings provide for a prosthetic implant comprising a femoral component, a tibial component, a bearing and a wear reduction device. The femoral component is operable to replace at least a portion of a patient's natural femur. The tibial component is operable to replace at least a portion of a patient's natural tibia, the tibial component having a superior tibial component surface. The bearing is operable to provide engagement between the femoral component and the tibial component. The bearing has a superior bearing surface operable to articulate with the femoral component and an inferior bearing surface operable to cooperate with the superior tibial component surface. The wear reduction device is located at least one of the superior tibial component surface and the inferior bearing surface and is operable to reduce wear upon at least one of the superior tibial component surface and the inferior bearing surface.

The present teachings also provide for a prosthetic tibial implant comprising a tibial plate and a stem. The tibial plate is operable to replace at least a portion of a patient's tibia. The tibial plate has a superior surface and an inferior surface opposite the superior surface, a bearing engagement surface located at the superior surface, and a wear reduction device located at the superior surface. The stem extends from the inferior surface.

The present teachings further provide for a prosthetic implant comprising a first member, a second member engaging the first member, and a wear reduction device provided on at least one of the first member and the second member to reduce wear of the first member and the second member.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present teachings will become more fully understood from the detailed description and the accompanying drawings, wherein.

DESCRIPTION OF VARIOUS EMBODIMENTS

The following description of the preferred embodiments is merely exemplary in nature and is in no way intended to limit the invention, its application, or uses.

Figure 1:
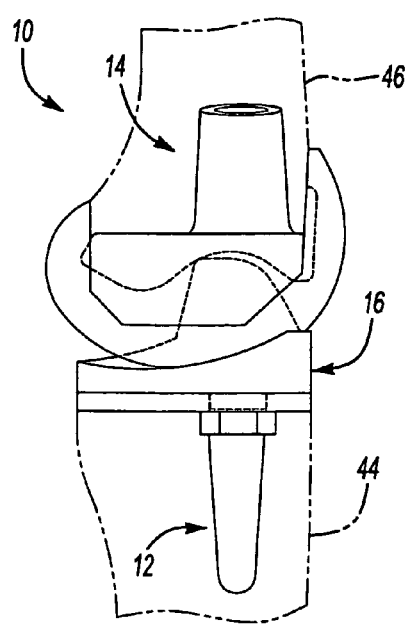
FIG. 1 is a partially cross-sectioned side view of a mobile bearing knee implant illustrated in accordance with the present invention.

With initial reference to FIG. 1, a knee implant exhibiting the present teachings is illustrated at reference numeral 10. While the present teachings are illustrated and described in terms of the knee implant 10, the present teachings may be implemented within a variety of different prosthetic implants. Further, while the knee implant 10 is illustrated as a mobile bearing knee implant, the knee implant 10 may be any type of implant, such as a posterior stabilized implant, a fixed bearing implant (FIG. 4), a fully constrained implant, a cruciate retaining implant, or a hinged implant.

Figure 2:
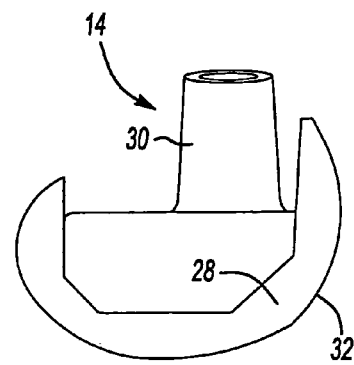
FIG. 2 is a partially cross-sectioned, exploded side view of the knee implant of FIG. 1.
Figure 2:
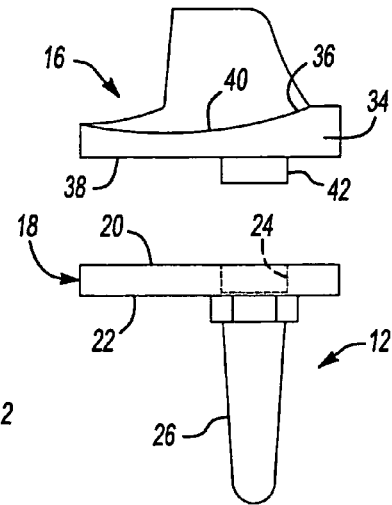
Figure 3:
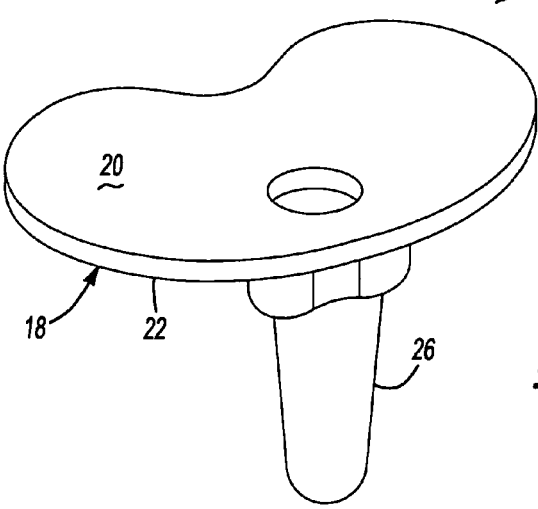
FIG. 3 is a perspective view of a tibial component of the knee implant of FIGS. 1 and 2.

With continuing reference to FIG. 1 and additional reference to FIGS. 2 and 3, the knee implant 10 generally can comprise a tibial component 12, a femoral component 14, and a mobile bearing 16. The tibial component 12 can generally include a tibial plate 18 having a superior tibial component surface 20 and an inferior surface 22. The superior surface 20 can be, for example, planar or concave and can include a bearing engagement surface 24. As illustrated, the bearing engagement surface 24 is recessed within the superior tibial component surface 20, however, the bearing engagement surface 24 can extend from the superior tibial component surface 20 or may be any type of receptor capable of cooperating with a corresponding receptor of the bearing 16. A tibial stem 26 can extend from the inferior surface 22. The tibial stem 26 can be secured to or within a bone surface to anchor the tibial component 12. The tibial stem 26 can be tapered such that the diameter of the stem 26 is smallest at a point furthest from the tibial plate 18. Further, the stem 26 can be a modular stem having different lengths that can be secured to the tibial plate 18. The tibial stem 26 can be made from any suitable biocompatible material, such as titanium.

The femoral component 14 can generally include a condyle portion 28 and an optional femoral stem 30 that can be modular. The condyle portion 28 can have an outer articulating surface 32. The outer articulating surface 32 can be a convex surface. The femoral stem 30 can extend from an undersurface of the articulating surface 32 to secure the femoral component 14 to bone. The femoral stem 30 can be tapered such that its diameter is smallest at a point furthest from the condyle portion 28. The femoral component 14 can be made from any suitable biocompatible material, such as titanium.

The bearing 16 can include a body 34 generally having a superior bearing surface 36 and an inferior bearing surface 38, which can be opposite the superior bearing surface 36. The inferior bearing surface 38 may be a convex surface when the superior surface 20 is concave to provide a wider range of movement between the bearing 16 and the tibial component 12. The superior bearing surface 36 can include a concave femoral receptor 40 operable to cooperate with the convex articulating surface 32 of the femoral component 14. The femoral receptor 40 can also have a convex outer surface, particularly when the articulating surface 32 is concave. The inferior bearing surface 38 can include a tibial receptor 42. The tibial receptor 42 can be any type of receptor suitable for cooperating with the tibial component 12. For example, the tibial receptor 42 can be a surface that extends from the inferior bearing surface 38 to cooperate with the bearing engagement surface 24 of the superior tibial component surface 20. The bearing 16 may be made from any suitable biocompatible component, such as polyethylene, a combination of metal and polyethylene, or entirely metal.

Figure 4:
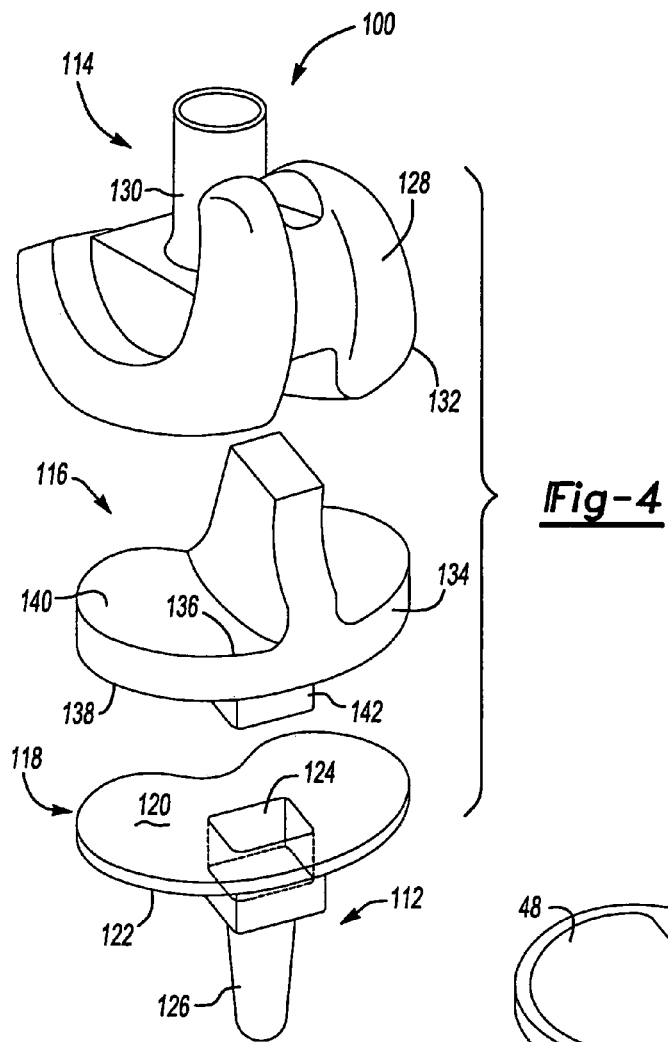
FIG. 4 is an exploded side view of a fixed bearing knee implant.

FIG. 4 illustrates a knee implant 100. The knee implant 100 is similar to the knee implant 10, the exception being that the implant 100 has a fixed bearing 116. Because the implant 100 is similar to the implant 10, the description of the implant 10 also applies to the implant 100 and need not be repeated. Components of the implant 100 that are similar to the components of the implant 10 are designated using the reference numbers of the implant 10 increased by 100. Because the implant 100 has a fixed bearing 116, the bearing engagement surface 124 is shaped to immovably secure the tibial receptor 142 within the bearing engagement surface 124.

With reference to FIGS. 1 through 3, the operation of the knee implant 10 will now be described. As the operation of the knee implant 10 is similar to the operation of the knee implant 100, the majority of the below description also applies to the implant 100. A tibia bone 44 can be prepared to receive the tibial component 12. Specifically, the tibial stem 26 can be received by a patient's natural tibia 44 and can be secured to or within the natural tibia using a suitable method or device, such as bone cement.

The tibial component 12 can mate with the bearing 16 through cooperation between the tibial receptor 42 of the bearing 16 and the bearing engagement surface 24 of the tibial component 12. As illustrated, the tibial receptor 42 extends from the inferior bearing surface 38 and is received by the bearing engagement surface 24. The tibial receptor 42 can be secured within the bearing engagement surface 24 using any suitable device or method, such as a morse taper fit. As illustrated in FIGS. 2 and 3, the tibial receptor 42 may rotate within the engagement surface 24 because the implant 10 is a mobile bearing system. In some applications, the receptor 42 can move within the engagement surface 24 in at least one of the anterior/posterior and medial/lateral directions. In other applications, such as the implant 100 illustrated in FIG. 4, the receptor 42 may be fixed within the engagement surface 24.

A femur bone 46 can be prepared to receive the femoral component 14. In particular, the femur 46 can be prepared to receive the femoral stem 30 of the femoral component 14. The femoral stem 30 can be secured to the femur using any suitable method or device, such as bone cement. The femoral component 14 cooperates with the bearing 16, which can be secured to the tibial component 12 as described above. Specifically, the articulating surface 32 of the femoral component 14 cooperates with the superior bearing surface 36 of the bearing 16. When the articulating surface 32 is a convex surface and the femoral receptor 40 is a concave surface, the articulating surface 32 can be seated within the femoral receptor 40, which can be recessed within the superior bearing surface 36. The femoral component 14 may be made from any suitable biocompatible material, such as titanium.

During operation of the knee implant 10, articulation between the femoral component 14 and the bearing 16 may cause the bearing 16 to move relative to the tibial component 12. Such movement can occur whether the bearing 16 is fixed to the tibial component 12 or mobile. This movement may result in wear of the inferior bearing surface 38 and/or the tibial component surface 20. To reduce wear, the tibial component surface 20 and/or the inferior bearing surface 38 can include one or more of a variety of different features or be subject to one or more of a variety of different treatments that can generally increase the hardness of the tibial component surface 20 and/or the inferior bearing surface 38 to prevent possible degradation of these surfaces. While the below description details treatment of the superior tibial component surface 20, such treatments can also be applied to the inferior bearing surface 38 as well as the inferior bearing surface 138 and the superior tibial component surface 120 of the implant 100 (FIG. 4).

Figure 5:
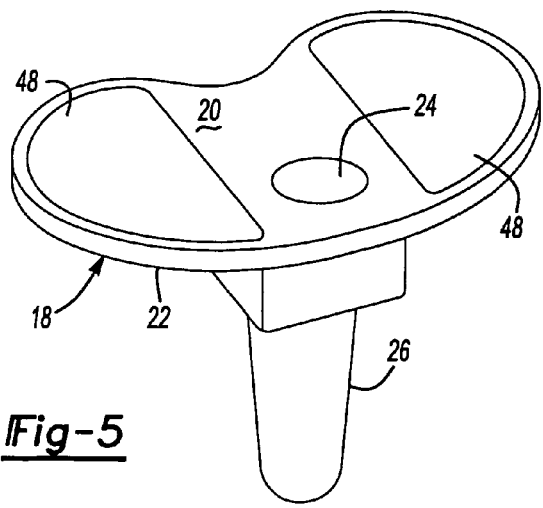
FIG. 5 is a perspective view of the tibial component of FIG. 3 outfitted with ceramic inserts.

As illustrated in FIG. 5, the superior tibial component surface 20 can include a ceramic surface 48. The ceramic surface 48 can be provided by a solid ceramic inlay of, for example, zirconia or alumina. The presence of the ceramic surface improves the wear resistance between the superior tibial component surface 20 and the inferior bearing surface 38. The ceramic surface 48 can be secured in place using one or more of a variety of suitable techniques or devices. For example, the ceramic surface 48 can be anchored using an adhesive, mechanical fixation, such as a taper fit, surface deformation so that portions of the tibial component surface 20 are manipulated or bent to hold the ceramic surface 48 in place, or the insertion of the ceramic surface 48 within a dovetail groove formed within the tibial component surface 20. The ceramic insert 48 can also be secured in position by using PVD deposition or a brazed alloy or oxide conversion. A niobium and hafnium alloy can also be used to form a metal oxide at the surface 20 to hold the insert 48 in position. Further, the insert 48 can include niobium and hafnium alloy, which can be oxidized to hold the insert 48 in position. Still further, titanium nitride or an oxidizable zirconium alloy can be used to treat the tibial component surface 20 to make the surface 20 resistive to wear or receptive to securing the ceramic surface 20.

According to the present teachings, the superior tibial component surface 20 can be modified by the diffusion of oxygen and/or nitrogen into the superior tibial component surface 20. This surface modification can be provided by fabricating the tibial component 12 out of an oxidizable alloy, such as tiodyne 3510, and then converting the superior tibial component surface 20 to an oxide. Also, the superior tibial component surface 20 can be nitrided by PVD coating, plasma source ion implantation, or ion nitriding. In some applications, the surface 20 is first cleaned using conventional cleaning techniques, such as plasma cleaning. The cleaned surface 20 is then heated and exposed to oxygen and/or nitrogen, which is absorbed by the cleaned surface 20. Modification of the superior tibial component 20 in any of the ways described above improves the wear resistance between the bearing 16 and the tibial component 12.

According to the present teachings, the superior tibial component surface 20 can be anodized using a type II conversion coating. Numerous conversion coatings can be used, such as type II tiodizing coatings. The use of conversion coatings can improve the surface roughness and increase the surface hardness of the superior tibial component surface 20. Anodizing the superior tibial component surface 20 can decrease the occurrence of wear between the tibial component surface 20 and the inferior bearing surface 38. Typically, the anodizing procedure involves anodizing the metal, such as titanium, of the surface 20 in a sodium phosphate bath and exposing the surface 20 to potential. The potential drives oxygen into the surface 20 to create the conversion coating.

According to the present teachings, the superior tibial component surface 20 can also be burnished to create a work hardened zone on the surface 20. The hardened zone can have an increased hardness that will improve the ability of the material to be polished and enhance the abrasion resistance of the alloy. The work hardened surface can be created using one or more of CO, CR, MO, and Ti-6-4. The work hardened zone also provides increased fatigue strength due, in part, to the compressive surface developed on the superior tibial component surface 20. Providing the superior tibial component surface 20 with such a work hardened zone can decrease the occurrence of wear between the tibial component surface 20 and the inferior bearing surface 38. The burnishing process can be carried out using a variety of conventional techniques. For example, burnishing can be performed using any method to deform the surface 20. Deformation of the surface 20 significantly hardens the surface 20 to provide increased resistance to wear. The surface 20 can also be work hardened by using, for example, a roller, laser shock processing, and/or a shock beam.

The above teachings are merely exemplary in nature and, thus, variations that do not depart from the gist of the teachings are intended to be within the scope of the teachings. Such variations are not to be regarded as a departure from the spirit and scope of the teachings.

What is claimed is:

1. A prosthetic implant comprising:
   a femoral component operable to replace at least a portion of a patient's natural femur;
   a tibial component operable to replace at least a portion of a patient's natural tibia, said tibial component having a superior tibial component surface;
   a bearing operable to provide engagement between said femoral component and said tibial component having:
      a superior bearing surface operable to articulate with said femoral component; and
      an inferior bearing surface operable to cooperate with said superior tibial component surface; and
   a wear reduction device located at at least one of said superior tibial component surface and said inferior bearing surface and operable to reduce wear upon at least one of said superior tibial component surface and said inferior bearing surface, said wear reduction device is coplanar with at least one of said superior tibial component surface and said inferior bearing surface;
   wherein said wear reduction device is a ceramic insert seated within a recess located at least one of said superior tibial component surface and said inferior bearing surface.

2. The implant of claim 1, wherein said bearing is fixed relative to said tibial component.

3. The implant of claim 1, wherein said bearing is movable relative to said tibial component in a medial to lateral direction.

4. The implant of claim 1, wherein said bearing is movable relative to said tibial component in an anterior to posterior direction.

5. The implant of claim 1, wherein said bearing is operable to move in a rotational direction relative to said tibial component.

6. The implant of claim 1, wherein said superior tibial component is planar.

7. The implant of claim 1, wherein said superior tibial component surface is at least one of a concave or a convex surface.

8. The implant of claim 1, wherein said ceramic insert is at least one of zirconia and alumina.

9. A prosthetic tibial implant comprising:
   a tibial plate operable to replace at least a portion of a patient's tibia having:
      a superior surface;
      an inferior surface opposite said superior surface;
      a bearing engagement surface located at said superior surface; and
      a wear reduction device located at said superior surface and coplanar with both said superior surface and said bearing engagement surface; and
   a stem extending from said inferior surface;
   wherein said wear reduction device is a ceramic insert seated within a recess at said superior surface.

10. The implant of claim 9, wherein said superior surface is planar.

11. The implant of claim 9, wherein said superior surface is curved.

12. The implant of claim 9, wherein said ceramic insert is at least one of zirconia and alumina.

13. A prosthetic implant comprising:
   a first member having a first surface;
   a second member with a second surface that engages said first surface of said first member; and
   a wear reduction device provided on and co-planar with at least one of said first surface and said second surface to reduce wear of said first member and said second member;
   wherein said wear reduction device is a ceramic insert seated within a recess in at least one of said first surface and said second surface.

14. The implant of claim 13, wherein said first member is a tibial component operable to replace at least a portion of a patient's natural tibia.

15. The implant of claim 14, wherein said second member is a bearing operable to permit articulation between a femoral component and said tibial component.

16. The implant of claim 13, wherein said first member is fixed relative to said second member.

17. The implant of claim 13, wherein said ceramic insert is at least one of zirconia and alumina.

18. The implant of claim 13, wherein said first member is movable relative to said second member.

* * * * *